United States Patent [19]

Greenberg

[11] 4,202,129

[45] * May 13, 1980

[54] INSECT-COMBATTING DEVICE

[75] Inventor: Jack Greenberg, Richmond, Va.

[73] Assignee: A. H. Robins Company, Inc., Richmond, Va.

[*] Notice: The portion of the term of this patent subsequent to Dec. 7, 1993, has been disclaimed.

[21] Appl. No.: 857,992

[22] Filed: Dec. 6, 1977

[51] Int. Cl.² .................. A01N 9/36; A01N 17/00
[52] U.S. Cl. .................................. 43/131; 424/78; 424/225
[58] Field of Search ............... 43/129, 131; 119/160, 119/106; 424/219, 225, 78

[56] References Cited
U.S. PATENT DOCUMENTS

| | | | |
|---|---|---|---|
| 2,971,882 | 2/1961 | Ospenson et al. | 424/225 |
| 3,882,226 | 5/1975 | Bradburne | 424/219 |
| 3,882,227 | 5/1975 | Bradburne | 424/219 |
| 3,996,348 | 12/1976 | Greenberg | 43/131 X |

Primary Examiner—Robert C. Watson

[57] ABSTRACT

An improved insect-combatting device (e.g., for use against houseflies, gnats and mosquitoes) is disclosed. The device comprises a shaped solid body having a porous surface capable of gradually and continually releasing naled insecticide in an amount sufficient to provide an insecticidally active concentration of said naled over a prolonged period of time and comprises a synthetic resinous matrix material, from about 15 to about 35 weight percent of naled and a minor amount effective to retard spewing of the insecticide of finely divided silica particles and at least one $C_{14}$ to $C_{20}$ saturated aliphatic carboxylic acid or a salt or ester thereof. The device is formed from a mixture of the said synthetic resin, naled, finely divided silica particles, $C_{14}$ to $C_{20}$ to aliphatic saturated carboxylic acid or salt or ester thereof and a surface porosity control component that is non-reactive in the mixture and has a boiling point at or below the curing temperature to produce surface openings in communication with pores in said body by vaporization of said porosity control component to provide the release of naled gas at a rate effective to control insects in the vicinity of said body, but insufficient to form as spew on the body.

10 Claims, 1 Drawing Figure

INSECT-COMBATTING DEVICE

BACKGROUND OF THE INVENTION

This invention relates to the control of insects such as common houseflies (*Musca domestica*), fruit flies (*Drosophila melanogaster*), mosquitoes (*Culex pipiens*) and other similar insects in the vicinity of an insecticide-containing device.

Heretofore, insect-combatting devices, such as pest strips and the like, comprised of a PVC resin having a dispersion of the insecticide dimethyl 2,2-di-chlorovinyl phosphate, commonly known as DDVP or by its trademark Vapona, have been widely used for the purpose of controlling flying insects such as houseflies, mosquitoes and the like in the vicinity of the device. However, DDVP has been reported to have an objectionable depressing effect on the plasma and red cell cholinesterase at least in animals which effect is particularly acute at high concentrations which are produced during the first few days after a pest strip has first been exposed to the atmosphere. This is believed due to the fact that the liberation rate of DDVP from presently available DDVP-containing pest strips is not uniform but rather is higher during the first few days after activation, i.e., removal of the pest strip from the packing and exposing it to the atmosphere. There are also indications that DDVP may be harmful to humans. Pest strips containing DDVP have been banned in Holland. Moreover, the aforementioned initial high liberation rate represents an unduly rapid loss of insecticide and creates an upper limit on the period that DDVP is liberated at a rate sufficient to effectively control pests. DDVP also has been found to possess a high degree of residual toxicity in the area of the device, apparently from adsorption of the DDVP vapors in walls, floors, ceilings, curtains, rugs, and the like. Even after a DDVP-containing pest strip is removed from a room environment, residual DDVP vapors can often be detected for several days thereafter.

It has also been suggested to utilize other insecticides such as naled (1,2-dibromo-2,2-dichloroethyl dimethyl phosphate) in an insect-combatting device such as a pest strip. The preparation of naled is described in U.S. Pat. No. 2,971,882 to Osmonson et al. PVC resin-naled combinations have been proposed for use as an insecticide of a general nature in French Pat. No. 1,568,198, issued Apr. 14, 1969, and in U.S. patent application Ser. No. 85,445, filed Jan. 30, 1961 (abandoned, but accessible to the public), and corresponding British Pat. No. 955,350. Netherlands published application No. 6,610,279 discloses fly strips composed of PVC-naled as well as PVC-DDVP combinations which are stated to have such high insecticide release rates as to require an outer laminate layer to retard the insecticide release. U.S. Pat. No. 3,344,021 discloses PVC-naled combinations for use as an anthelmintic composition.

A number of problems have been encountered in providing a commercially satisfactory PVC resin-naled combination for use in an insect-combatting device. First, there must be a sufficient amount of naled released to provide effective control of the insects in the vicinity of the device. Contrary to statements in the prior art disclosures, it has been found that release rates for naled are very much less than the release rates for DDVP. Naled has a low vapor pressure of about $2 \times 10^{-4}$ mm. Hg. at 20° C. as compares to that for DDVP of $1.2 \times 10^{-2}$ to be thus only about 1.7% of the vapor pressure of DDVP.

It has further been found that the inclusion of an insecticide such as naled in a synthetic resin matrix in amounts sufficient to control insects for a commercially acceptable time leads to exudation of liquid insecticide (or "spew") on the surface of the device. These liquid droplets pose serious environmental and aesthetic problems as well as significantly decreasing the effective life of the device.

A further unexpected problem found with a PVC-naled composition was the tendency of the resin to decompose during the shaping process. For example, unsatisfactory results were obtained in early tests where naled was substituted for DDVP in PVC combinations employed in extrusion apparatus used for making PVC-DDVP pet collars known in the art. Burning and charring of the extrudate were found to occur during curing of the collars, and the finished collar underwent an unexplainable reduction in the naled concentration as compared with the naled concentration in the original mixture.

In U.S. Pat. No. 3,996,348, the disclosure of which is herein incorporated by reference, there is disclosed and claimed an efficacious body for combatting insects. The particular shaped body shown therein is in the form of a hexagonal or honeycomb structure which has an advantageous mass to surface area ratio.

OBJECTS AND SUMMARY OF THE INVENTION

It is an object of this invention to provide an insect-combatting device and method of using said device which alleviates or avoids the problems of the prior art.

A further object of this invention is to provide an insect-combatting device which may contain a relatively high loading of insecticide without objectionable liquid insecticide droplet formation on the surface of the device and a method of using such device.

It is also an object of this invention to provide an insect-combatting device which is capable of combatting insects in the vicinity of the device by prolonged release of insecticide while minimizing undesired adsorption of the insecticide into contiguous solid objects and a method of using said device.

A further object of the invention is to provide a method of combatting insects by making a body of synthetic resin containing between about 15% and 35% of naled through the use of a volatile additive which is released during the curing step to produce a texture including porous surface openings which allow for an unexpectedly large increase in the release of naled gas at a rate effective to control insects to thus provide a naled-containing device which has a commercially practical effective life.

Another object of the invention is to provide a shaped body having a structure which is readily adapted to commercial molding operations while still maintaining an advantageous mass to surface area ratio.

The present invention provides a device for combatting insects comprising a shaped solid body having a porous surface capable of gradually and continually releasing naled insecticide in an amount sufficient to provide an insecticidally active concentration of said naled over a prolonged period of time, said device comprising a synthetic resinous matrix material, from about 15 to about 35 weight percent of naled and a minor amount effective to retard spewing of the insecticide of finely divided silica and at least one $C_{14}$ to $C_{20}$ saturated aliphatic carboxylic acid or a salt or ester thereof, said device being formed from a mixture of said synthetic resin, naled, finely divided silica particles, $C_{14}$ to $C_{20}$ aliphatic saturated carboxylic acid or salt or ester thereof and a surface porosity control component that is non-reactive in the mixture and has a boiling point at or below the curing temperature to produce surface opening in communication with pores in said body by vaporization of said porosity control component to provide for release of naled gas at a rate effective to control insects in the vicinity of said body, but insufficient to form as spew on the body, said shaped body having a plurality of cavities which extend entirely through one dimension of said body, said cavities having sustantially parallel axes.

BRIEF DESCRIPTION OF THE DRAWING

The FIGURE is a schematic representation of a preferred embodiment of the insect-combatting device of the present invention.

DESCRIPTION OF THE PREFERRED EMBODIMENTS

Figure 1:
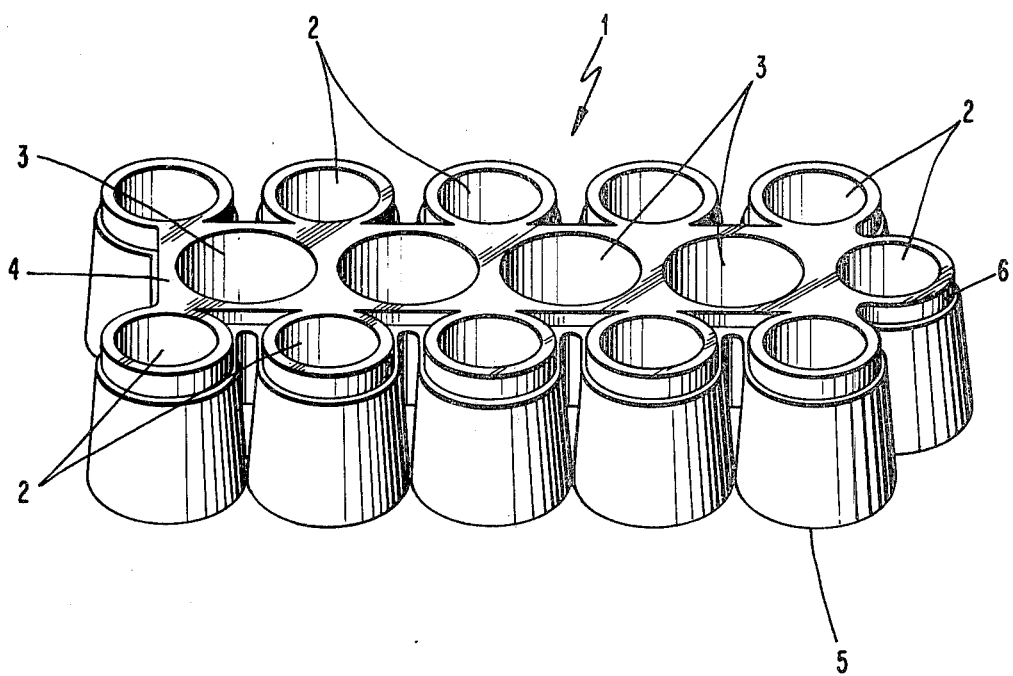

Referring now to the drawing, FIG. 1 shows a preferred device for combatting insects. As shown therein, the device is in the form of a shaped body 1 having a plurality of cavities generally indicated as 2 and 3 which extend throughout one dimension of the body. As further shown therein, the cavities may be circular in cross-section and formed in two series of cavities with one series of cavities being greater in cross-section (i.e., diameter) than the other series of cavities. Preferably, the plurality of smaller diameter cavities is disposed about the plurality of greater diameter cavities.

The cavities 2, 3 have substantially parallel axes and are each tapered in cross-section from one side 4 of the body 1 to the other side 5 of the body. The use of tapered walls has been found to be particularly advantageous in the molding of the shaped body, particularly in promoting the release of the shaped body from the mold. In addition, the utilization of the tapered walls allows the body to have an advantageous mass (about 100 g.) to surface area (about 55–60 in²) ratio while retaining good air circulation through the shaped body.

The side of the body having the smallest diameter of the holes 2 and 3 may also be provided with a reduced portion 6 which further enhances the mold release action of the shaped body.

The components making up a satisfactory insecticide-containing insect-combatting device include a synthetic resin that is compatible with the relatively high amounts of insecticide and a strength sufficient to maintain the integrity of the shaped device throughout the period during which the insecticide is released in amounts effective to combat insects, e.g., flies or mosquitoes. The shaped insect-combatting device includes the synthetic resin in a concentration sufficiently large to give the device physical properties such as strength, flexibility, and freedom from tackiness so as to make it suitable for use as an insect-combatting device. Generally, the shaped device contains from about 20 to about 80, preferably from about 25 to about 50, weight percent of the synthetic resin.

The various known synthetic resins which can be used in the insect-combatting device include materials such as polyethylene, polypropylene, copolymers of ethylene and propylene, nylon, cellophane, polyacrylates, such as polymers and copolymers of methylacrylate, ethylacrylate, methylmethacrylate and ethylmethacrylate; polymers of vinyl compounds, such as polystyrene, polymerized divinylbenzene; polyvinyl halogenides, such as polyvinylchloride; polyvinyacetals, such as polyvinylbutyral; polyvinylidene compounds, such as polyvinylidenechloride; polyvinylacetate; ethylvinylacetate-vinylacetate copolymers; copolymers of vinylchloride and vinylacetate; polyurethanes, polyaldehydes; and ethermoplastics.

Polyvinylchloride (PVC) homopolymers and copolymers with other polymers such as polyvinyl acetate (PVA) are preferred synthetic resin materials. Suitable PVC resins are commercially available and include, for example, PVC homopolymer dispersion resin Diamond PVC-7502$^{TM}$ and PVC homopolymer extender resin Diamond PVC-7-446$^{TM}$, both available from the Diamond Shamrock Co., and mixtures thereof. Other suitable, commercially available PVC resins are known in the art. Suitable PVC-PVA copolymers are also commercially available and include, for example, Geon 135 (Goodrich Corp.), PVC-74 (Diamond Alkali Co.) and XR-6338 (Exxon-Firestone). Other PVC-PVA copolymers are also known in the art.

The improved insect-combatting device of the present invention contains naled (1,2-dibromo-2,2-dichloroethyl dimethyl phosphate) insecticide in an amount sufficient to provide an insecticidally active concentration of the insecticide over a prolonged period of time (e.g., about 120 days or longer), which amount can be from about 15 to about 35, preferably from about 20 to about 30, weight percent insecticide. With insecticide concentrations in these ranges, the insect-combatting device releases from about 1.5 to about 5 milligrams of insecticide per inch of surface area per day. Although the insect-combatting device of the present invention may be utilized in any environment containing the insects, maximum efficiency may be obtained when the device is utilized in a confined space including these insects.

Generally, the utilization of naled insecticide in amounts of from about 15 to about 35 weight percent in a synthetic resin matrix leads to liquid naled droplet or "spew" formation on the surface of the insect-combatting device. Liquid droplets of naled insecticide forming on the surface of the shaped device pose a substantial health and safety hazard as well as diminished insecticidal efficiency. The insect-combatting device of the present invention includes a minor amount effective to retard spewing of the insecticide of finely divided silica particles and at least one $C_{14}$ to $C_{20}$ saturated aliphatic carboxylic acid or a salt or ester thereof and exhibits a substantially lessened tendency towards formation of liquid droplets of naled insecticide on its surfaces.

Although silica is known in the art, along with a number of other minerals and glasses, as a filler for various synthetic resins, it has unexpectedly been found that finely divided silica particles generally having a particle size of from about 1 to about 50, preferably from about 2 to about 10 microns, exhibit a high degree of relative efficiency in retarding insecticide spewing when utilized in sufficient amounts, which spew-retarding amounts are generally in the range of from about 10 to about 35, preferably from about 15 to about 25, weight percent of the insect-combatting device. It has been found that utilization of finely divided silica particles in an amount of less than about 10 percent by weight is generally ineffective to provide any significant retardation of the insecticide spew while utilization of finely divided silica particles in an amount above about 35 percent by weight does not result in any further reduction in spew formation.

While the addition of the finely divided silica particles exhibit a high degree of relative efficiency in retarding naled insecticide spewing, a small amount of the naled insecticide may nonetheless sometimes exude from the insecticide-containing device. It has further been found that the inclusion in the device of a minor amount of at least one $C_{14}$ to $C_{20}$ saturated aliphatic carboxylic acid, or a salt or ester (e.g., magnesium stearate) thereof, is effective to essentially retard any naled insecticide spewing which might otherwise occur. The $C_{14}$ to $C_{20}$ saturated aliphatic carboxylic acid, which can be a mixture of such acids, is generally utilized in an amount of from about 0.25 to about 3, preferably from about 0.5 to about 1.5, weight percent in the device. Stearic acid and palmitic acid are preferred.

While East German Pat. No. 91,898 discloses the addition of a $C_{14}$ to $C_{20}$ saturated aliphatic carboxylic acid along with a particular mixture of primary and secondary plasticizers to a polyvinyl chloride-DDVP mixture, the acid-plasticizers mixture being added to retard spewing of the DDVP, it has been found that the utilization of the $C_{14}$ to $C_{20}$ saturated aliphatic carboxylic acid alone (i.e., without the finely divided silica particles) with the resin and insecticide in the insect-combatting device of the present invention is insufficient to effectively retard spewing of the naled insecticide from the device. Similarly, the use of the finely divided silica particles alone (i.e., without the $C_{14}$ to $C_{20}$ saturated aliphatic carboxylic acid) is insufficient to effectively retard spewing of the insecticide from the device. However, the utilization of a minor amount of both the finely divided silica particles and the $C_{14}$ to $C_{20}$ saturated aliphatic carboxylic acid has been found to possess a high efficiency for insecticide spew retardation and to effectively maintain the surface of the device free of liquid droplets of the insecticide.

It has been ascertained that when the release rate falls off to about 0.4 to about 0.6 milligrams of naled per square inch of surface area per day, that the effectiveness of the device for insect control has been reduced to the point where it should be replaced. Utilization of naled in the device in amounts less than about 20 weight percent results in the release rate reaching an ineffective level in an unsatisfactorily short period of time (e.g., about 90 days or less). Utilization of naled in amounts greater than about 35 weight percent results in spewing and droplet accumulation on the surface of the device.

The preparation of synthetic resin-insecticide combinations is achieved by conventional methods. Because of the compatibility of the insecticide in the resin dispersions, the compositions may be prepared merely by mechanical mixing of the pesticides with powdered resin. Dry blends, fluid pastes, or plastisol dispersions, can be made which, as is known, can be molded, extruded, cast, or otherwise formed into the shape of a band or strip. Where the prepolymerized resin exists in liquid form, as in the case of such monomers as styrene or methyl methacrylate, the insecticide may be incorporated in the liquid before it is polymerized or cured. The term "dispersion" as used herein is intended to include mixtures of a solid with a liquid, a liquid with a liquid and a solid with a solid.

In the embodiments where polyvinyl resins are used, plasticizers and other additives commonly used for providing the flexibility, strength and surface characteristics desired for an insect-combatting device are well known to those skilled in this art, and no further discussion is deemed necessary here. In addition, coloring and odor control agents may be employed in the devices of the present invention to enhance consumer acceptance.

As noted above, naled has a low vapor pressure. The naled release rate from a PVC-naled device is comparatively low and may be inadequate for a commercially acceptable insect-combatting device. The use of an additive in the mixture can be very helpful in increasing the naled release rate and makes possible both effective insect control at lower initial naled concentrations and an insect-combatting device having an increased effective life.

The additive, also referred to as a surface porosity control component, is present in the final plastisol dispersion or mix used in forming the device, and hence must be non-reactive with the other components of the dispersion or mix. The main function of the additive is to provide a surface porosity which preferably includes pores extending part way into the body of the device. The desired surface characteristics are obtained by the vaporization of the additive during the curing period. Hence the additive should comprise one or more compounds having a boiling point at or below the curing temperature of the resin.

Compounds which are suitable as the surface porosity control component in PVC resins which are cured at a temperature in the range of between about 260° to 400° F. include aldehydes and their lower alkyl acetals containing bromine or chlorine, generally having a boiling point of from about 170° to about 400°, preferably from about 185° to about 350° F. The porosity control component may thus include one or more of the following which have approximate boiling point temperature as set forth:

| Name | B.F. °F. |
|---|---|
| chloroacetaldehyde | 185 |
| dichloroacetaldehyde | 192 |
| chloral | 218 |
| bromoacetaldehyde | 176–221 |
| dibromoacetaldehyde | 346 |
| bromodichloroacetaldehyde | 258 |
| chlorodibromoacetaldehyde | 299 |
| bromochloroacetaldehyde | 233 |
| 2-bromopropanol 229 | |

The surface porosity control component is included in the synthetic resin-naled combination in an amount sufficient to produce sufficient surface porosity by its vaporization during curing of the dispersion to effectively increase the release rate of naled gas from the formed device. While the amount of the porosity control component to be used depends on the density of surface openings desired and somewhat on the particular procedure used for curing the resin, it is generally from about 0.8 to 5, preferably from about 1 to 3, weight percent of the dispersion.

The invention is additionally illustrated in connection with the following Examples which are to be considered as illustrative of the present invention. It should be understood, however, that the invention is not limited to the specific details of the Examples.

EXAMPLE I

A mixture (in parts by weight) of the materials of Example I of U.S. Pat. No. 3,996,348 is thoroughly triturated to form a plastisol dispersion having a viscosity at 25° C. of 16,000 cps. as measured on a Brookfield viscometer at 20 rpm., 12,000 at 2 rpm. A portion of the plastisol is metered to a closed machined aluminum cast mold having a cavity as in the FIGURE. Temperature of the mold at filling time, as indicated by a thermocouple immediately beneath the cavity surface is 390° F. The mold temperature is maintained at 390° F. for 2.5 minutes to maintain the dispersion at or above the curing temperature, after which the mold temperature is lowered rapidly to ambient temperature. The color of the device is brownish bronze. A strong medicinal odor emanating from the finished resin is detected.

Analysis of the device after curing and cooling shows the naled content of the device to be 26% by weight.

The device, when tested for efficacy against flies, shows a killing power of the same order as the shaped body of U.S. Pat. No. 3,996,348.

EXAMPLE II

The mixture and procedure of Example I is repeated except that 30 weight percent of a technical grade of naled (1,2-dibromo-2,2-dichloroethyl dimethyl phosphate) commercially available from the Chevron Chemical Company is used. This product is known to contain certain impurities such as bromodichloroacetaldehyde, chloral, carbon tetrachloride and various forms of phosphates. These impurities constitute about 9 weight percent of the product and in large part are sufficiently volatile as to be released during the curing of the device or shortly thereafter and hence not to interfere with the funcitoning of the device.

The device formed and cured in the manner indicated in Example I is brownish bronze and contains about 26 weight percent naled. Again, the efficiency of fly kill is similar to that obtained in U.S. Pat. No. 3,996,548.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A device for combatting insects comprising a shaped solid body having a porous surface capable of gradually and continually releasing naled insecticide in an amount sufficient to provide an insecticidally active concentration of said naled over a prolonged period of time, said device comprising a synthetic resinous matrix material, from about 15 to about 35 weight percent of naled and a minor amount effective to retard spewing of the insecticide of finely divided silica particles and at least one $C_{14}$ to $C_{20}$ saturated aliphatic carboxylic acid or a salt or ester thereof, said device being formed from a mixture of said synthetic resin, naled, finely divided silica particles, $C_{14}$ to $C_{20}$ aliphatic saturated carboxylic acid or salt or ester thereof and a surface porosity control component that is non-reactive in the mixture and has a boiling point at or below the curing temperature to produce surface opening in communication with pores in said body by vaporization of said porosity control component to provide for release of naled gas at a rate effective to control insects in the vicinity of said body, but insufficient to form as spew on the body, said shaped body having a plurality of cavities which extend entirely through one dimension of said body, said cavities having substantially parallel axes.

2. The shaped body of claim 1 wherein said cavities have walls which are tapered from one side of said body to the opposite side of said body.

3. The shaped body of claim 1 wherein said cavities are circular in cross-section.

4. The shaped body of claim 3 wherein said plurality of cavities includes a first plurality of cavities and a second plurality of cavities, said first plurality of cavities having a diameter greater than those of the second plurality of cavities.

5. The shaped body of claim 4 wherein said second plurality of cavities are disposed about the first plurality of cavities.

6. The device of claim 1 wherein the silica particles are present in an amount of from about 10 to about 35 weight percent of said device and said acid is present in an amount of from about 0.25 to about 3 weight percent of said device.

7. The shaped body of claim 1 wherein said synthetic resinous matrix material is a polyvinyl chloride.

8. The shaped body of claim 1 wherein said mixture contains a minor amount of a surface porosity control component having a boilingpoint of from about 170° F. up to the curing temperature of the polyvinyl chloride synthetic resinous material.

9. The shaped body of claim 8 wherein said surface porosity control component is selected from the group consisting of chloroacetaldehyde, dichloroacetaldehyde, chloral, bromoacetaldehyde, dibromoacetaldehyde, bromal, bromodichloroacetaldehyde, chlorodibromoacetaldehyde, bromochloroacetaldehyde, 2-bromopropanol and mixtures thereof.

10. A method of controlling insects which comprises:
providing a discrete body, said shaped body having a plurality of cavities which extend entirely through one dimension of said body, said cavities having substantially parallel axes comprising a mixture of a synthetic resin, from between about 15 to 35% by weight of said strip of naled and a spew retarding amount of finely divided silica particles and at least one $C_{14}$ to $C_{20}$ saturated aliphatic carboxylic acid or a salt or ester thereof;
said body being formed from a mixture of said synthetic resin, naled, silica particles, saturated aliphatic carboxylic acid and a minor amount of a surface porosity control agent that is non-reactive in the mixture and has a boiling point at or below the curing temperature of said mixture, which mixture is formed into said body at the curing temperature to vaporize said control agent and produce surface porosity in said body to provide for release of naled at a rate to effectively control insects in the vicinity of said body but insufficient to form as droplets on the body; and
placing and maintaining said body in an area in which said insects are to be controlled.

* * * * *